United States Patent [19]

Clement

[11] Patent Number: 5,118,507
[45] Date of Patent: Jun. 2, 1992

[54] SILICONE BASED COSMETIC COMPOSITION

[75] Inventor: Pamela A. Clement, Huntington, Conn.

[73] Assignee: Elizabeth Arden Co., Division of Conopco, Inc., New York, N.Y.

[21] Appl. No.: 720,358

[22] Filed: Jun. 25, 1991

[51] Int. Cl.⁵ .................. A61K 7/02; A61K 7/42
[52] U.S. Cl. ...................... 424/401; 424/59; 514/63
[58] Field of Search .............. 424/401, 78, 59

[56] References Cited

U.S. PATENT DOCUMENTS

| | | | |
|---|---|---|---|
| 4,246,257 | 1/1981 | Elliott et al. | 424/78 |
| 4,370,319 | 1/1983 | Chapin et al. | 424/184 |
| 4,515,784 | 5/1985 | Bogardus et al. | 514/63 |
| 4,678,663 | 7/1987 | Scott et al. | 424/62 |
| 4,826,828 | 5/1989 | Wilmott et al. | 514/63 |
| 4,888,363 | 12/1989 | Dulak et al. | 514/725 |
| 4,911,925 | 8/1990 | Shatkina et al. | 424/401 |
| 4,950,688 | 8/1990 | Bowser et al. | 514/847 |

*Primary Examiner*—Thurman K. Page
*Assistant Examiner*—Neil Levy
*Attorney, Agent, or Firm*—Milton L. Honig

[57] ABSTRACT

A cosmetic composition is provided that includes a volatile silicone fluid, a non-volatile silicone gum and a $C_{16}$-$C_{22}$ fatty acid ester of citric acid. The composition is particularly intended for application to areas surrounding the eyes.

11 Claims, No Drawings

SILICONE BASED COSMETIC COMPOSITION

BACKGROUND OF THE INVENTION

1. Field of the Invention

The invention relates to a cosmetic composition for application to the skin, especially for treatment in areas surrounding the eyes.

2. The Related Art

Reduction or, at least, covering of facial lines and wrinkles is an important function of a cosmetic skin composition. Nowhere on the face is this function more important than around the area of the eyes. Signs of aging are particularly evident in this region.

In formulating a composition for application around the eye area, consideration must not only be given to anti-aging actives but also to aesthetics of the product. These products must be sufficiently thick to avoid running of the material into the corneum which would cause irritation. These products must stay in place even in high-heated environments. Not all types of thickening agents can be successfully employed for such products. For instance, certain types of traditional thickening agents are quite temperature sensitive with respect to viscosity. Most important, however, is that a great many thickening agents and, even cosmetic vehicles, impart the wrong feel to the skin.

U.S. patent application Ser. No. 588,249, now U.S. Pat. No. 5,063,057 (Spellman et al) discloses formulations where the vehicle and thickener may be silicone oils or gums. High viscosity silicones are known to thicken a formulation but leave a slippery residue thereby imparting a slippery rather than a tacky feel. Consumers find this undesirable. Instead, a tacky residue has been found through consumer testing to be the most aesthetically pleasing.

Another desirable aesthetic of a skin care product is to have a clear or transparent composition. Not all thickening agents and/or vehicles are sufficiently compatible or of the proper refractive index to achieve product clarity.

Accordingly, it is an object of the present invention to provide a skin care product that includes both volatile components and relatively non-volatile ones, with the latter conveying a slightly tacky feel to the skin upon evaporation of the lower boiling components.

Another object of the present invention is to provide a skin care product especially suitable for use in areas surrounding the eyes.

A further object of the present invention is to provide a skin care product sufficiently thick so as to prevent the product from running once placed upon the skin.

A still further object of the present invention is to provide a skin care product that is clear or transparent.

Other objects, features and advantages will become more readily apparent upon reference to the summary and detailed description of the invention that follows.

SUMMARY OF THE INVENTION

A cosmetic product is provided comprising:
(i) from about 1 to about 90% of a volatile silicone fluid;
(ii) from about 0.1 to about 20% by weight of a non-volatile silicone gum; and
(iii) from about 0.5 to about 50% of a $C_{16}$-$C_{22}$ fatty acid ester of citric acid.

DETAILED DESCRIPTION

Now it has been discovered that certain types of citrate esters can be formulated with silicones to provide not only a clear composition but one that leaves a slightly tacky consumer-appealing residue upon evaporation of volatile ingredients from the silicone formulation.

Thus, an essential component of the composition of the present invention is a $C_{16}$-$C_{22}$ fatty acid ester of citric acid. Illustrative of the citrate esters are triisostearyl citrate, tristearyl citrate, diisostearyl citrate, monoisostearyl citrate, distearyl citrate, monostearyl citrate, trilinoleayl citrate, tripalmitoyl citrate and mixtures thereof. These esters may be present in amounts ranging from about 0.5 to about 50%, preferably from about 5 to about 30%, optimally between about 15 and 20% by weight.

Another important component of the present invention is that of a volatile silicone carrier. Particularly suitable are the polyalkyl siloxanes and the polyalkyl phenyl siloxanes. Low viscosity or volatile polydimethyl siloxanes are available as cyclomethicone in pentamer and/or tetramer form, often present as 9:1 blends. Viscosities of the volatile silicones may range from about 0.5 to less than 10 centistokes at 25° C. Concentrations of these silicones may range from about 1 to about 90%, preferably from about 20 to about 50% by weight.

A third component of compositions of this invention will be a non-volatile silicone gum. These gums will normally be polyalkyl siloxanes with a viscosity ranging from about 10 up to about 10,000,000 centistokes at 25° C. Polydimethyl siloxanes of high viscosity are available commercially under the trademarks SE 30 Gum. and Vicasil from the General Electric Company. Concentrations of the silicone gum may range from about 0.1 up to about 20%, preferably from about 0.5 to about 2%, optimally about 1% by weight.

Mixtures of high and low viscosity polydimethyl siloxanes are commercially available, one such example being Dow Corning X2-1146A Fluid.

Advantageously the compositions of the present invention are substantially anhydrous, i.e. containing less than about 2%, preferably less than about 0.5% water.

Best results have been achieved where the ratio of silicone gum to citrate ester has ranged from about 1:10 to about 1:100, preferably between about 1:15 and about 1:30, optimally about 1:18.

Various types of active ingredients may be present in cosmetic compositions of the present invention. Actives are defined as skin or hair benefit agents other than emollients and other than ingredients that merely improve the physical characteristics of the composition. Although not limited to this category, general examples include sunscreens and skin anti-wrinkling agents.

Sunscreens include those materials commonly employed to block ultraviolet light. Illustrative compounds are the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the emulsions can vary depending upon the degree of protection desired from the sun's UV radiation.

Anti-wrinkling agents are best exemplified by the 2-hydroxyalkanoic acids, prostaglandins, retinoic acids, ceramides and their derivatives. These agents may be present anywhere from about 0.00001 to about 5%, preferably from about 0.0001 to about 1%, optimally between about 0.01 and 0.2% by weight of the total composition. Most preferred of the active compounds mentioned above is 2-hydroxyoctanoic acid, retinol or retinyl palmitate and pigskin or bovine-brain lipid ceramides. Further identification of ceramide structures may be found in U.S. Pat. No. 4,950,688 (Bowser et al), herein incorporated by reference.

Other adjunct minor components may also be included in the cosmetic compositions. These ingredients may include preservatives, coloring agents, opacifiers and perfumes. Amounts of these materials may range anywhere from 0.001 up to 20% of the composition.

Compositions of the claimed invention may be packaged in a variety of different delivery systems. For instance, the systems may include aerosol spray devices, brush-applicator devices, impregnated pads, roll-on bottles and capsules. Most preferred of these systems are capsules such as those disclosed in U.S. application Ser. No. 588,249 now U.S. Pat. No. 5,063,057 (Spellman). The preferred capsules have a round body with hollow chamber forming a major portion of the capsule, a tab forming a minor portion of the capsule, and a neck section connecting the tab with the round body. Upon twisting, the neck can be broken to allow release of the cosmetic compositions of the present invention from within the chamber. For optimum aesthetics, the capsule wall is transparent thereby emphasizing the transparent nature of the composition of this invention. Walls of the capsule may be formed from any transparent material including but not limited to transparent gelatin, polyvinyl alcohol or polyvinyl pyrrolidone.

The following examples will more fully illustrate selected embodiments of this invention. All parts, percentages and proportions referred to herein and in the appended claims are by weight unless otherwise indicated.

EXAMPLE 1

A cosmetic composition illustrative of the present is described in the Table below.

| Phase | Ingredient | Wt. % |
|-------|------------|-------|
| A | Silicone Fluid 344 | 51.974 |
|   | Silicone Fluid 345 | 20.000 |
|   | Silicone Gum SE-30 | 1.000 |
| B | Tri Isostearyl Citrate | 18.000 |
|   | Jojoba Oil | 3.000 |
|   | Caprylic/capric Triglyceride | 3.000 |
| C | Witch Hazel Extract | 1.000 |
|   | Nettle Extract | 1.000 |
|   | Filagrinol | 0.500 |
|   | Phytantriol | 0.200 |
|   | Vitamin E Linoleate | 0.100 |
|   | Rose Hips Oil | 0.100 |
|   | Cucumber extract | 0.100 |
|   | 1% Ceramide I in Squalene | 0.025 |
|   | Vitamin K-1 | 0.001 |

A composition was prepared by charging a sanitized stainless steel tank provided with a propeller mixer with Silicone Fluid 344 and Silicone Fluid 345 (cyclomethicone). Silicone Gum SE-30 was then slowly added to the stirred silicone fluid mixture. The composition was further stirred to achieve complete uniformity so that no gum pieces remained thereby forming a phase A. In a separate tank equipped with a propeller mixer, the citrate, jojoba oil and caprylic/capric triglyceride were mixed together to form a phase B solution. All remaining ingredients (phase C) in the above Table were then combined with phase B and the resultant solution agitated until uniform. Phase A was then added to the combined phases B and C followed by sufficient agitation to achieve a uniform composition.

EXAMPLE 2

This Examples reports a series of experiments to identify additives which could impart a consumer-desired tacky afterfeel to an essentially silicone vehicle. The following base formula was employed as the vehicle in testing the various additives:

| Vehicle Component | Wt. % |
|-------------------|-------|
| Silicone Gum SE-30 | 10.0 |
| Silicone Fluid 345 | 20.0 |
| Silicone Fluid 344 | 58.5 |

A series of additives were incorporated into this base silicone formulation. Results of skin feel tests on the additive incorporated base formula are reported below.

| Additive (CTFA Name) | Result |
|----------------------|--------|
| Diglyceryl diisostearate | Insoluble - 2 layers formed |
| Diisostearyl fumarate | Insoluble - 2 layers formed |
| Triisostearyl trimerate | Cloudy |
| Maleated soybean oil | Insoluble - 2 layers formed |
| Lanolin oil | Milky |
| PEG45/Dodecyl glycol copolymer | Cloudy |
| Purified ester gum | Milky, thick |
| Dimethicone/trimethylsiloxysilicate | Clear but insufficient afterfeel |
| Diisostearyl maleate | Clear but insufficient afterfeel |
| Triisostearyl citrate | Clear, good afterfeel |

Evident from the above Table is that only triisostearyl citrate provided both a clear transparent solution and also one that had a good afterfeel (tackiness).

EXAMPLE 3

A series of formulations were prepared to evaluate the effect of relative concentrations between silicone gum and triisostearyl citrate. The compositions utilized the base formula as outlined under Example 1. Afterfeel performance experiments indicated that the best ratio of silicone gum to triisostearyl citrate was 1:18. Satisfactory results were, however, also found for these material where the relative ratio ranged from 1:10 to 1:20. See Table below.

TABLE
Effect of Silicone Gum to Citrate Ratio

| Sample No. | % Silicone Gum | % Triisostearyl Citrate | Performance |
|------------|----------------|-------------------------|-------------|
| 1 | 10.0 | 30.0 | Rub-in time too long; too much emollient feel |
| 2 | 10.0 | 20.0 | Spreading into eyes; too little afterfeel |
| 3 | 5.0 | 25.0 | Slight draggy afterfeel |
| 4 | 10.0 | 25.0 | Less residual afterfeel than |
| 5 | 15.0 | 25.0 | Too thick |
| 6 | 5.0 | 15.0 | Too little afterfeel |

TABLE-continued

Effect of Silicone Gum to Citrate Ratio

| Sample No. | % Silicone Gum | % Triisostearyl Citrate | Performance |
|---|---|---|---|
| 7 | 1.0 | 18.0 | Excellent afterfeel |
| 8 | 1.0 | 20.0 | Good afterfeel |
| 9 | 1.0 | 10.0 | Adequate afterfeel |
| 10 | 5.0 | 36.0 | Very draggy afterfeel |

The foregoing description and examples illustrate selected embodiments of the present invention and in light thereof variations and modifications will be suggested to one skilled in the art, all of which are within the spirit and purview of this invention.

What is claimed is:

1. A cosmetic composition comprising:
   (i) from about 1 to about 90% of a volatile silicone fluid;
   (ii) from about 0.1 to about 20% by weight of a non-volatile silicone gum; and
   (iii) from about 0.5 to about 50% of a $C_{16}$–$C_{22}$ fatty acid ester of citric acid, said non-volatile silicone gum and fatty acid ester of citric acid being present in a relative ratio of about 1:10 to about 1:20.

2. A composition according to claim 1 wherein said volatile silicone fluid has a viscosity ranging from about 0.5 to less than 10 centistokes at 25° C.

3. A composition according to claim 1 wherein said non-volatile silicone gum has a viscosity ranging from about 10 up to about 10,000,000 centistokes at 25° C.

4. A composition according to claim 1 wherein said citrate ester is triisostearyl citrate.

5. A composition according to claim 1 wherein said composition is substantially anhydrous such that there is less than about 2% water present.

6. A composition according to claim 1 further comprising from about 0.00001 to about 5% by weight of a ceramide selected from the group consisting of pigskin lipid ceramides, bovine-brain lipid ceramides and mixtures thereof.

7. A composition according to claim 1 further comprising an active ingredient from about 0.0001 to about 5% by weight of 2-hydroxyoctanoic acid.

8. A composition according to claim 1 further comprising from about 0.00001 to about 5% by weight of retinol and ester derivatives thereof.

9. A composition according to claim 1 which is clear.

10. A cosmetic composition comprising:
    (i) from about 1 to about 90% of a volatile silicone fluid;
    (ii) from about 0.1 to about 20% by weight of a non-volatile silicone gum; and
    (iii) from about 0.5 to about 50% of a $C_{16}$–$C_{22}$ fatty acid ester of citric acid, said composition including less than about 2% water.

11. A clear cosmetic composition comprising:
    (i) from about 1 to about 90% of a volatile silicone fluid;
    (ii) from about 0.1 to about 20% by weight of a non-volatile silicone gum; and
    (iii) from about 0.5 to about 50% of a $C_{16}$–$C_{22}$ fatty acid ester of citric acid which is a triisostearyl citrate, said non-volatile silicone gum and citrate being present in a ratio of about 1:10 to about 1:20.

* * * * *